United States Patent [19]

Kaliman et al.

[11] Patent Number: 5,269,751
[45] Date of Patent: Dec. 14, 1993

[54] THROMBECTOMY CATHETER FOR ENLARGING AN ARTERY

[76] Inventors: Josef Kaliman, Haizingergasse 54/2/1, A-1180 Wien; Alfred Wichart, Burggasse 76, A-1070 Vienna, both of Austria

[21] Appl. No.: 918,942

[22] Filed: Jul. 22, 1992

Related U.S. Application Data

[63] Continuation of Ser. No. 851,272, Mar. 13, 1992, abandoned, which is a continuation of Ser. No. 675,027, Mar. 25, 1991, abandoned, which is a continuation of Ser. No. 410,704, Sep. 21, 1989, abandoned.

[30] Foreign Application Priority Data

Sep. 21, 1988 [AT] Austria .................................. 2316/88

[51] Int. Cl.[5] ............................................ A61B 17/22
[52] U.S. Cl. ........................................ 604/22; 606/159
[58] Field of Search ................ 606/159, 180; 604/22; 128/751-755

[56] References Cited

U.S. PATENT DOCUMENTS

| | | | |
|---|---|---|---|
| 3,320,957 | 5/1967 | Sokolik | 606/180 |
| 4,700,705 | 10/1987 | Kensey et al. | 606/159 |
| 4,728,319 | 3/1988 | Masch | 604/22 |
| 4,772,258 | 9/1988 | Marangoni et al. | 606/159 X |
| 4,857,046 | 8/1989 | Stevens et al. | 604/22 |
| 4,886,490 | 12/1989 | Shiber | 604/22 |
| 4,895,560 | 1/1990 | Papantonakos | 606/159 X |

FOREIGN PATENT DOCUMENTS 0191630 8/1986 European Pat. Off. .

Primary Examiner—Michael M. Thaler
Attorney, Agent, or Firm—Herbert Dubno

[57] ABSTRACT

A thrombectomy catheter has a flexible twisted guide probe along which the catheter tube and tool can be threaded into an artery and which is driven by its end remote from an exploratory finger formed by the guide probe and projecting beyond a cutting tool at the end of the tube. The guide probe delivers torque to the tool to rotate the latter thereby eliminating the need to extract the guide probe from the tube and insert a separate drive element.

6 Claims, 3 Drawing Sheets

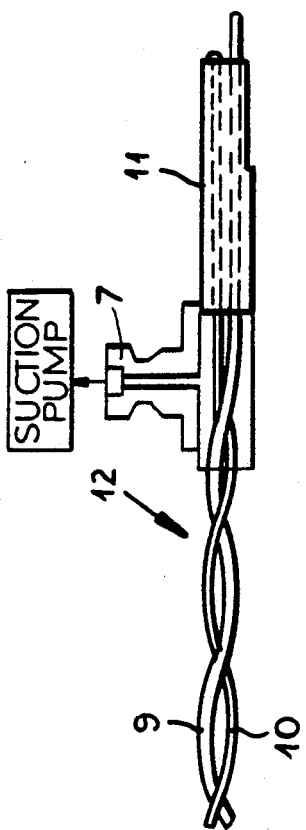
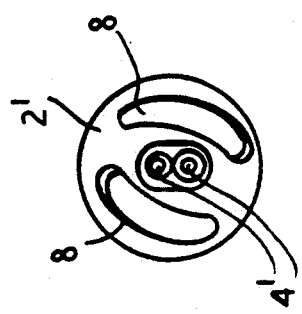
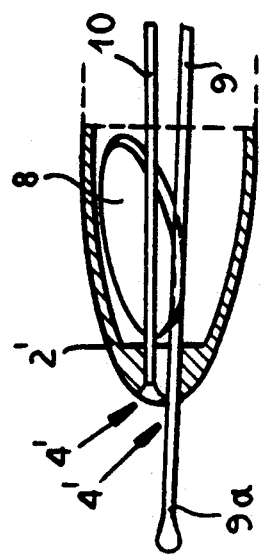
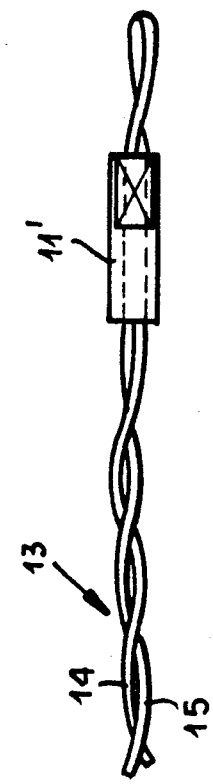
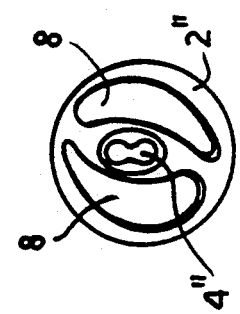
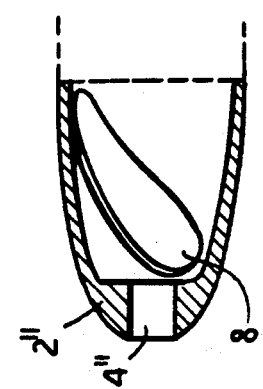

THROMBECTOMY CATHETER FOR ENLARGING AN ARTERY

This is a continuation of co-pending application Ser. No. 07/851,272 filed on Mar. 13, 1992 which is a continuation of Ser. No. 07/675,027 filed Mar. 25, 1991 which is a continuation of Ser. No. 07/410,704 filed Sep. 21, 1989 all of which are now abandoned.

FIELD OF THE INVENTION

My present invention relates to a thrombectomy catheter for enlarging the flow cross section or lumen of an artery which may be constricted by an arterial sclerotic condition. More particularly the invention relates to a catheter for this purpose which comprises a tube which may be guided on a probe inserted into the artery and carrying at its forward end a tool, such as a drilling or milling tool, for cutting away obstructive tissue.

BACKGROUND OF THE INVENTION

It is known to enlarge the lumen or flow cross section of an artery by the use of a thrombectomy catheter which has a drilling or milling tool rotatable, e.g. by an electric motor, and a tube at the end of which the tool is provided.

A guide probe can be inserted into the artery and can include one or more wires to serve as a guide for this tube. For this purpose the tool can have a passage extending axially therethrough to enable relative axial movement of the tool and tube on the guide probe.

For exact guidance and positioning of the thrombectomy catheter in the artery to be subjected to thrombectomy, the guide probe is initially inserted into the artery and the movement of the guide probe therealong is monitored by radiography, e.g. X-ray.

In a conventional embodiment of the thrombectomy catheter, as soon as the guide probe reaches an arterial constriction or blockage, a tube is passed over the guide probe to that constriction or obstruction, the tube having at its leading end a tool having an axial bore.

The guide probe is then retracted from the artery through the tube and a flexible drive shaft is inserted into the tube. The drive shaft comprises a coupling member at its leading end which engages in a corresponding countermeasure of the tool in an indexing manner.

When the drive shaft is coupled with the tool, the tool is set into rotation via the drive shaft and is advanced together with the tube to enlarge the lumen of the artery by a cutting operation.

This thrombectomy catheter is indeed effective although its use is time-consuming because it requires threading the tube onto the guide probe, withdrawal of the guide probe, threading a -drive shaft through the tube and like operations which are time-consuming. Furthermore, some of these operations may be threatening to the well-being of the patient.

U.S. Pat. No. 4,700,705 describes a thrombectomy catheter having a tool at the leading end of a tube. The tool here is formed with a cylindrical axial bore through which a guide probe can be fed. The drive of the tool head, however, is effected by a separate drive shaft coaxial with the guide probe.

This construction is relatively complex. Furthermore, because of the complex mechanism, there is no free space for a circulation of the blood and for the transportation of excised material from the constriction or obstruction.

Similar problems are encountered with the catheter of European patent publication EP-0 191 630 in which the drive of the tool is effected by a turbine directly adjacent the tool itself.

OBJECTS OF THE INVENTION

It is, therefore, the principal object of the present invention to provide a thrombectomy catheter which is free from the drawbacks enumerated above.

More specifically, it is an object of the invention to provide a thrombectomy catheter which can be used more rapidly and with less threat to the patient and especially which can avoid the need for withdrawal of the guide probe and insertion of a flexible drive shaft into a previously positioned tube.

Another important object of this invention is to provide a thrombectomy catheter which is of relatively simple construction and provides free space for the circulation of blood or the removal of excised material.

Yet a further object of this invention is to provide an improved highly reliable and easily handled thrombectomy catheter.

SUMMARY OF THE INVENTION

These objects and others which will become apparent hereinafter are attained, in accordance with the invention, by forming the guide probe and the drive shaft as one and the same part. According to the invention, therefore, the guide probe means remains in place within the tube and the tool and the passage in the tool couples the tool to the guide probe means rotationally but allows the probe to be axially displaceable on the probe.

Alternatively, a guide probe wire is provided with a further wire parallel to the guide probe wire. This further wire is coupled to the tool to transfer torque thereto from an electric motor at a remote extremity of the guide probe means, at least in part by twisting this further wire around the first-mentioned wire. In either case, preferably a twist is imparted to the guide probe means and the guide probe projects beyond the tool, for example by 0.5 to 2 cm, to provide a guiding function and to support the cross section-enlargement function of the tool.

In the construction of the invention, the guide probe can remain within the tube and need not be extracted therefrom. The guide probe means has a cross section differing from a circular cross section to effect the torque transfer to the tool. This deviation from the circular by the guide probe means cross section can result from constituting the guide probe means as a single wire with a noncircular cross section or combinations of wires which can have circular cross sections. In either case, the passage in the tool should have a cross section corresponding to the cross section of the guide probe to enable the tool and tube to be slid along the guide probe outside the patient and also to provide a reliable and directly controllable angular coupling between the guide probe and the tool without impeding axial shiftability of the tube and guide probe relative to one another.

Because of the simplified construction of the catheter, the tool as well as the tube can provide space for circulation and removal of blood and excised tissue.

This applies as well to the embodiment of the invention in which, parallel to a guide-probe element or wire, within the tube, an additional wire engages the tool. This additional wire serves as a torque-transmission member and is angularly coupled to the tool.

The guide probe, after the tube and tool have been threaded thereover into the artery, can be connected with a controlled-speed electric motor drive and, together with the additional wire, can provide the function of a drive shaft for the tool.

The advance of the thrombectomy catheter through the artery is effected during the rotation of the tool together with the guide probe. As in the first-mentioned embodiment, the leading end of the latter can project forwardly beyond the front face of the tool.

As a consequence, the projecting end of the guide probe acts as an exploratory finger which tends to engage in the remaining passage of a constricted artery.

To a certain extent, the exploratory finger, during the rotation, acts as an excising tool to enlarge flow cross section of the artery in advance of the cutting tool.

In a particular embodiment of the invention, the guide probe has a rectangular cross section and is twisted over its length within the tube and externally thereof. This twisted rectangular cross section, effectively provides a screw within the tube which promotes displacement of the liquid phase toward the rear of the catheter and thus assists in movement of the evacuated blood and excised solids in the direction of a suction port provided at the rear end of the catheter. The screw surface is formed by the band-shaped guide probe during the rotation.

While the twist can be established only upon application of torque to the tool, it has been found to be advantageous to provide the guide probe with a twist in advance of its insertion into the artery and the application of the tube thereover. In this case, the sense of rotation is so selected with respect to the hand of the twist that the liquid material and entrained solids will be displaced toward the rear end of the catheter.

A similar effect ca be obtained when the guide probe is constituted of at least two individual wires lying alongside one another, even when each of them is of circular cross section.

The individual wires can be two conventional probe wires of, however, different diameters.

One of the wires can be a relatively thin wire closely wound around the relatively thick wire to form the twist. The two wires lie against one another and collectively have the cross section of a figure eight. A corresponding passage in the tool also has this shape.

One of the wires can be somewhat longer than the other to provide the function of the aforedescribed exploratory finger while the other wire or wires can extend only to the end face of the tool. The wires can be axially shiftable independently from one another.

As soon as the wires are set in rotation, they generate the screw-like twist previously described. High torque can be transferred in this manner. The longer of the two wires can thus form the guide-probe member while the shorter terminates at the tool and engages the latter in a torque-transmitting fashion.

In another embodiment of the invention, the individual wires forming the guide-probe means can be twisted together in advance of the application of torque to form a screw-conveyor surface conveying the liquid and entrained solids to the outlet of the tube. The device thus forms a worm conveyor for this purpose.

The guide probe is, according to the invention, non-rotatably anchored in an entrainment at the rear end but longitudinally shiftable therein while the entrainer is driven by an electric motor.

In more general terms, the invention thus comprises a thrombectomy catheter which includes:

flexible elongated guide-probe means insertable into an artery and having a twisted configuration along a length thereof for guiding the catheter into and along the artery;

a flexible tube surrounding the elongated guide-probe means and having an end terminating short of a leading end of the guide-probe means, whereby the leading end of the guide-probe means projects beyond the end of the tube to guide the tube through the artery and to facilitate lumen enlargement by the catheter;

a tool on the end of the tube having cutting formations and rotatable to cut through obstructions in the artery to enlarge the lumen thereof, the tool being operatively coupled to the guide probe means so that the tool is rotatably driven by the guide-probe means, the guide-probe means extending through the tool and projecting therebeyond; and a drive operatively coupled to the guide probe means at an extremity thereof opposite the leading end for rotating the guide probe means and thereby drive the tool.

BRIEF DESCRIPTION OF THE DRAWING

The above and other objects, features and advantages of the present invention will become more readily apparent from the following description, reference being made to the accompanying drawing in which:

FIG. 2a is a cross-sectional view through a milling cutter which can be used as a tool at the end of a thrombectomy catheter according to the invention;

FIG. 2b is a front elevational view of this tool;

FIG. 2c is a side elevational view of a drive shaft/guide probe as used to drive this tool and guide the thrombectomy catheter for the tool of FIGS. 2a and 2b;

FIG. 2d is a cross sectional view through the guide probe;/drive shaft of FIG. 2c;

FIGS. 3a–3d are views similar to FIGS. 2a–2d illustrating another embodiment of the invention.

SPECIFIC DESCRIPTION

Figure 1:
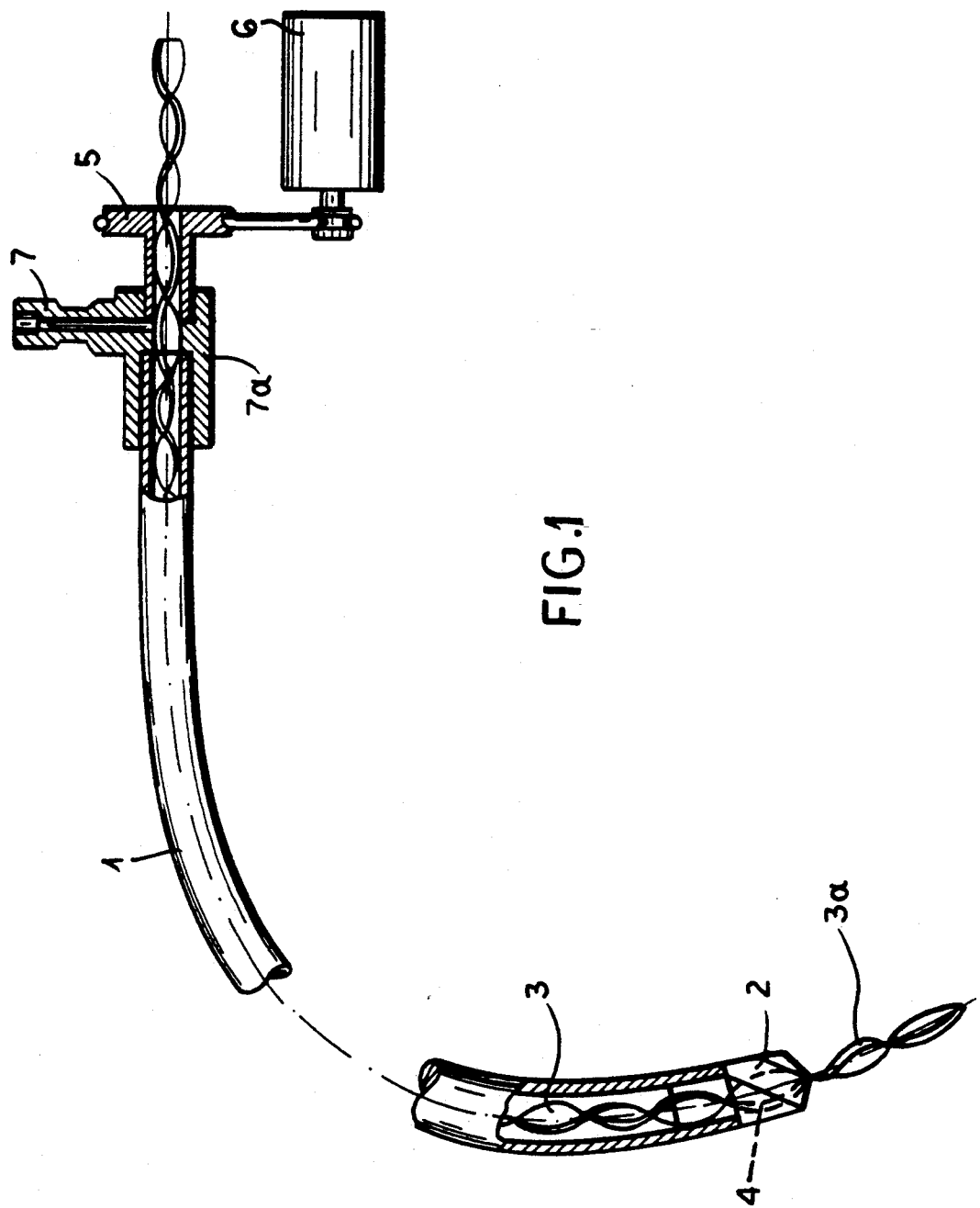
FIG. 1 is an elevational view of a thrombectomy catheter according to the invention together with its drive, partially broken away.

The thrombectomy catheter shown in FIG. 1 comprises a flexible tube 1 and a tool 2 rotatably mounted at the free end of the tube 1. The tool 2 is here shown as a drill bit. Within the tube 1, a guide probe 3 extends.

According to the invention, the flexible guide probe 3 is inserted into an artery and the tube 1 with the tool 2 is thereafter shoved over the guide probe 3 until the tool 2 reaches the constriction or obstruction to be excised For this purpose the tool 2 has an axial throughgoing passage 4.

The guide probe 3 has a cross-sectional shape which differs from the circular and in the embodiment of FIG. 1 is rectangular. The guide probe 3 is also twisted to form a screw surface. The passage 4 in the tool 2 or a part of this passage also has this cross section so that the tool 2 is angularly coupled to the guide probe 3 although it is axially shiftable thereon.

At the opposite extremity of the thrombectomy catheter, an entrainer 5 is angularly coupled to the guide probe 3 and has the configuration of a pulley connected by a belt transmission to an electric motor 6 forming an electromotor drive.

The fitting 7 of a housing 7a communicating with the rearward extremity of the tube 1 is connectable to a suction pump (not shown) so that the blood and entrained excised solids from drilling through the constricted or obstructed artery can be drawn off.

After a corresponding processing to remove the entrained solids, the blood or blood fluids can be recirculated to the patient.

The rotation of the screw formed by the twisted guide probe 3 advances the blood along the tube 1 to its right-hand or rear end for evacuation. The direction of rotation of the guide probe imparted by the electromotor drive 6 is so selected with respect to the hand of the twist that the rotation of the screw promotes by screw-conveyer action the displacement of the liquid and entrained solids to the fitting 7.

Figure 4A:
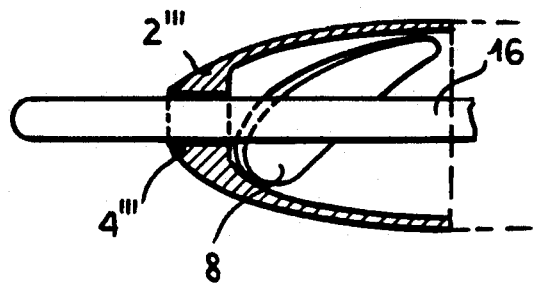
FIGS. 4a–4d are views similar to FIGS. 2a–2d, respectively, illustrating still another embodiment.
Figure 4B:
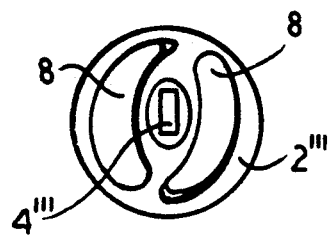
Figure 4C:
Figure 4D:

The tool 2, like the tools 2', 2" and 2''' shown in FIGS. 2a, 3a and 4a, can be provided with openings 8 which permit the liquid and entrained solids to be sucked into the tool and the tube.

While the guide probe is formed in FIG. 1 from a single flattened flexible wire and has a leading end 3a projecting some 0.5 to 2 cm beyond the free end of the tube and its tool to act as an exploratory finger, the guide probe shown in FIGS. 2a-2c comprises two individual wires 9 and 10 represented in combination at 12 and having circular cross sections.

In this embodiment, the relatively heavy wire 9 forms the exploratory finger at 9a (FIG. 2a) while the wire 10, which wraps in a twist around the wire 9, forms together therewith a drive shaft.

The tool 2' and the associated tube (not shown) can be axially shoved over the wire 9 to follow the latter into the artery. The free end of the wire 10 in its axial bore 4' is fixed at the front of the tool 2' while the wire 9 passes axially freely through its passage 4'.

The catheter can be inserted into the artery in such manner that the two wires are initially parallel to one another. The two wires are, however, angularly connected to an entrainer 11 which may be coupled with a pulley such as that shown at 5 to enable the combination 12 to be rotated. When the drive 6 is turned on, therefore, the wires 9 and 10 are twisted together in the manner illustrated in FIG. 2c to impart torque to the rotatable tool 2'.

Projecting portions 9a of the wire 9 thus functions as an exploratory finger and also serves to promote the lumen-widening effect of the tool 2' in the manner described.

As illustrated in especially FIG. 3c in the embodiment of FIGS. 3a-3d, a guide probe 13 is provided which consists of previously twisted wires 14 and 15. In this embodiment, the passage 4" has a form-fitting configuration with respect to the twisted wires so that the tool 2" is rotatably driven when the entrainer 11' is rotated.

In a further embodiment represented in FIGS. 4a-4d, a flat flexible strip 16 forms the guide probe and can be previously twisted to have the screw configuration shown or can be twisted when set into rotation by the entrainer 11" and the drive 6. In this case, a generally elliptical passage 4''' is provided to receive the probe 16 and ensure angular entrainment of the tool 2''' when the strip 16 is rotated by the drive.

When the guide probe is constituted of a plurality of individual wires, these may have rectangular or circular cross sections. The important point, of course, is that the assembly have a cross section differing from the circular and enabling the application of torque to the tool when the guide probe is driven in the manner described.

I claim:

1. A thrombectomy catheter for enlarging the lumen of an artery constricted by arteriosclerosis, comprising:

flexible elongated guide probe means insertable into an artery for guiding said catheter into and along the artery;

a flexible tube surrounding said elongated guide probe means and having an end terminating short of a leading end of said guide probe means, whereby said leading end of said guide probe means projects beyond said end of said tube to guide said tube through said artery and to facilitate lumen enlargement by the catheter;

a tool on said end of said tube having cutting formations and rotatable to cut through obstructions in said artery to enlarge the lumen thereof, said leading end of said guide probe means having a unitary portion extending through said tool and axially movable relative to said tool to project therebeyond, said unitary portion having a cross section other than circular at said leading end for coupling in a corresponding cross section shaped passage of said tool to drive said tool; and a drive operatively coupled to said guide probe means at an extremity thereof opposite said leading end for rotating said guide probe means and thereby drive said tool, said guide probe means consisting of a single elongated element having a rectangular cross section and having a twist such that, upon rotation of said element, said element displaces liquid and entrained solids from a region of excision at said tool through said tube toward said extremity.

2. The thrombectomy catheter defined in claim 1 wherein said unitary portion extends substantially 0.5 to 2 cm from said tool at said leading end and said passage is provided at said leading end.

3. The thrombectomy catheter defined in claim 2 wherein said drive is an electric motor operatively connected to said extremity.

4. The thrombectomy catheter defined in claim 2 wherein said tool is a drill bit.

5. The thrombectomy catheter defined in claim 2 wherein said tool is a milling cutter.

6. The thrombectomy catheter defined in claim 1 wherein said passage is generally elliptical.

* * * * *